United States Patent [19]
Odorzynski et al.

[11] Patent Number: 5,879,341
[45] Date of Patent: Mar. 9, 1999

[54] ABSORBENT ARTICLE HAVING A BREATHABILITY GRADIENT

[75] Inventors: Thomas Walter Odorzynski, Green Bay; Joel Scott Sherman, Neenah, both of Wis.

[73] Assignee: Kimberly-Clark Worldwide, Inc., Neenah, Wis.

[21] Appl. No.: 622,903

[22] Filed: Mar. 29, 1996

[51] Int. Cl.$^6$ ..................................................... A61F 13/15
[52] U.S. Cl. ............................................................. 604/367
[58] Field of Search ............................................... 604/367

[56] References Cited

U.S. PATENT DOCUMENTS

| | | |
|---|---|---|
| 2,068,997 | 1/1937 | Spanel . |
| 2,068,998 | 1/1937 | Spanel . |
| 2,544,069 | 3/1951 | Cutler . |
| 2,604,097 | 7/1952 | White . |
| 2,649,859 | 8/1953 | Hermanson et al. . |
| 2,664,895 | 1/1954 | Shulman . |
| 2,675,805 | 4/1954 | Trimble . |
| 2,896,626 | 7/1959 | Voigtman . |
| 2,897,108 | 7/1959 | Harwood . |
| 2,897,109 | 7/1959 | Voigtman . |
| 2,964,040 | 12/1960 | Ashton et al. . |
| 3,004,895 | 10/1961 | Schwartz . |
| 3,156,242 | 11/1964 | Crowe, Jr. . |
| 3,315,676 | 4/1967 | Cooper . |
| 3,402,715 | 9/1968 | Liloia et al. . |
| 3,426,754 | 2/1969 | Bierenbaum et al. . |
| 3,463,154 | 8/1969 | Hendricks . |
| 3,559,649 | 2/1971 | Grad et al. . |
| 3,559,650 | 2/1971 | Larson . |
| 3,570,491 | 3/1971 | Sneider . |
| 3,676,242 | 7/1972 | Prentice . |
| 3,695,967 | 10/1972 | Ross . |
| 3,779,246 | 12/1973 | Mesek et al. . |

(List continued on next page.)

FOREIGN PATENT DOCUMENTS

| | | |
|---|---|---|
| 1 146 298 | 5/1983 | Canada . |
| 1 182 603 | 2/1985 | Canada . |
| 1 189 252 | 6/1985 | Canada . |
| 1 204 557 | 5/1986 | Canada . |
| 1 222 103 | 5/1987 | Canada . |
| 1 252 952 | 4/1989 | Canada . |
| 1 255 577 | 6/1989 | Canada . |
| 2023038 | 2/1991 | Canada . |
| 2008440 | 3/1991 | Canada . |
| 1 285 129 | 6/1991 | Canada . |
| 2024472 | 6/1991 | Canada . |
| 1291326 | 10/1991 | Canada . |
| 1311181 | 12/1992 | Canada . |
| 1312426 | 1/1993 | Canada . |
| 2088218 | 7/1993 | Canada . |
| 2068491 | 11/1993 | Canada . |
| 2116081 | 6/1995 | Canada . |

(List continued on next page.)

OTHER PUBLICATIONS

Derwent World Patent Database abstract of JP 6–910: Description of Kao Corp., "Porous Sheet Useful For Absorption Article Such As Disposable Diaper."

Primary Examiner—Mark O. Polutta
Attorney, Agent, or Firm—Jeffrey B. Curtin

[57] ABSTRACT

An absorbent article includes a garment facing surface which includes a first zone of vapor permeability which defines a water vapor transmission rate of from about 100 to about 2500 g/sq.m/24 hr and a second zone of vapor permeability which defines a water vapor transmission rate of at least about 3000 g/sq.m/24 hr. The article may include a substantially liquid impermeable, vapor permeable backsheet, a liquid-permeable topsheet positioned in facing relation with the backsheet, an absorbent body located between the backsheet and topsheet, and a vapor permeable barrier layer located between the absorbent body and the backsheet. The barrier layer is smaller in size than the backsheet. In such a configuration, the first zone of vapor permeability comprises the portion of the backsheet which overlays the barrier layer and the second zone of vapor permeability comprises the portion of the backsheet which extends beyond the barrier layer.

51 Claims, 2 Drawing Sheets

U.S. PATENT DOCUMENTS

| | | | |
|---|---|---|---|
| 3,881,489 | 5/1975 | Hartwell . | |
| 3,882,871 | 5/1975 | Taniguchi . | |
| 3,903,889 | 9/1975 | Torr . | |
| 3,911,186 | 10/1975 | Trotman | 428/137 |
| 3,932,682 | 1/1976 | Loft et al. . | |
| 3,989,867 | 11/1976 | Sisson . | |
| 4,015,604 | 4/1977 | Csillag . | |
| 4,059,114 | 11/1977 | Richards . | |
| 4,138,459 | 2/1979 | Brazinsky et al. . | |
| 4,196,245 | 4/1980 | Kitson et al. . | |
| 4,241,462 | 12/1980 | Tagawa et al. . | |
| 4,289,832 | 9/1981 | Schwarz . | |
| 4,306,559 | 12/1981 | Nishizawa et al. . | |
| 4,333,463 | 6/1982 | Holtman . | |
| 4,338,371 | 7/1982 | Dawn et al. . | |
| 4,341,216 | 7/1982 | Obenour . | |
| 4,376,147 | 3/1983 | Byrne et al. . | |
| 4,379,192 | 4/1983 | Wahlquist et al. . | |
| 4,384,024 | 5/1983 | Mitchell et al. . | |
| 4,411,660 | 10/1983 | Dawn et al. | 604/396 |
| 4,427,408 | 1/1984 | Karami et al. | 604/393 |
| 4,480,000 | 10/1984 | Watanabe et al. . | |
| 4,522,203 | 6/1985 | Mays | 128/132 D |
| 4,522,874 | 6/1985 | Pommez | 428/284 |
| 4,546,029 | 10/1985 | Cancio et al. . | |
| 4,578,066 | 3/1986 | O'Connor | 604/366 |
| 4,606,970 | 8/1986 | Sharps, Jr. . | |
| 4,609,584 | 9/1986 | Cutler et al. | 428/156 |
| 4,610,681 | 9/1986 | Strohbeen et al. | 604/396 |
| 4,623,340 | 11/1986 | Luceri . | |
| 4,626,252 | 12/1986 | Nishizawa et al. | 604/370 |
| 4,627,847 | 12/1986 | Puletti et al. | 604/366 |
| 4,632,860 | 12/1986 | D'Antonio et al. | 428/290 |
| 4,639,949 | 2/1987 | Ales et al. | 2/400 |
| 4,648,876 | 3/1987 | Becker et al. | 604/370 |
| 4,681,578 | 7/1987 | Anderson et al. | 604/385 R |
| 4,681,793 | 7/1987 | Linman et al. | 428/138 |
| 4,692,161 | 9/1987 | Puletti et al. | 604/366 |
| 4,713,068 | 12/1987 | Wang et al. | 604/366 |
| 4,713,069 | 12/1987 | Wang et al. | 604/378 |
| 4,718,898 | 1/1988 | Puletti et al. | 604/366 |
| 4,725,473 | 2/1988 | Van Gompel et al. | 428/156 |
| 4,734,324 | 3/1988 | Hill . | |
| 4,758,239 | 7/1988 | Yeo et al. | 604/366 |
| 4,777,073 | 10/1988 | Sheth | 428/155 |
| 4,798,602 | 1/1989 | Laus | 604/372 |
| 4,798,603 | 1/1989 | Meyer et al. | 604/378 |
| 4,818,600 | 4/1989 | Braun et al. | 428/290 |
| 4,822,350 | 4/1989 | Ito et al. | 604/372 |
| 4,822,435 | 4/1989 | Igaue et al. . | |
| 4,824,718 | 4/1989 | Hwang | 428/284 |
| 4,828,556 | 5/1989 | Braun et al. | 604/365 |
| 4,851,470 | 7/1989 | George . | |
| 4,883,480 | 11/1989 | Huffman et al. | 604/385.1 |
| 4,887,602 | 12/1989 | O'Leary | 604/305.1 |
| 4,902,553 | 2/1990 | Hwang et al. | 428/156 |
| 4,929,303 | 5/1990 | Sheth . | |
| 4,935,021 | 6/1990 | Huffman et al. | 604/385.1 |
| 5,026,591 | 6/1991 | Henn et al. . | |
| 5,062,839 | 11/1991 | Anderson | 604/385.1 |
| 5,069,678 | 12/1991 | Yamamoto et al. | 604/385.1 |
| 5,085,654 | 2/1992 | Buell | 604/370 |
| 5,098,423 | 3/1992 | Pieniak et al. | 604/385.1 |
| 5,114,418 | 5/1992 | Levy | 604/365 |
| 5,171,239 | 12/1992 | Igaue et al. | 604/385.2 |
| 5,176,668 | 1/1993 | Bernardin | 604/368 |
| 5,176,672 | 1/1993 | Bruemmer et al. | 604/385.1 |
| 5,188,626 | 2/1993 | Toyoda et al. | 604/385.1 |
| 5,192,606 | 3/1993 | Proxmire et al. | 428/284 |
| 5,208,098 | 5/1993 | Stover . | |
| 5,223,311 | 6/1993 | Tsutsumi et al. . | |
| 5,263,948 | 11/1993 | Karami et al. | 604/383 |
| 5,263,949 | 11/1993 | Karami et al. | 604/383 |
| 5,292,316 | 3/1994 | Suzuki | 604/385.2 |
| 5,342,469 | 8/1994 | Bodford et al. . | |
| 5,364,381 | 11/1994 | Soga et al. | 604/366 |
| 5,385,972 | 1/1995 | Yamamoto et al. . | |
| 5,409,761 | 4/1995 | Langley . | |
| 5,451,467 | 9/1995 | Lock . | |
| 5,507,736 | 4/1996 | Clear et al. | 604/385.2 |
| 5,523,146 | 6/1996 | Bodford et al. . | |
| 5,560,974 | 10/1996 | Langley . | |
| 5,571,096 | 11/1996 | Dobrin et al. | 604/383 |
| B1 4,636,207 | 11/1989 | Buell | 604/370 |
| B1 4,662,875 | 4/1989 | Hirotsu et al. | 604/389 |

FOREIGN PATENT DOCUMENTS

| | | |
|---|---|---|
| 0 104 906 B1 | 4/1984 | European Pat. Off. . |
| 0 269 401 A3 | 6/1988 | European Pat. Off. . |
| 0 283 200 A3 | 9/1988 | European Pat. Off. . |
| 0 360 929 A1 | 4/1990 | European Pat. Off. . |
| 0 457 905 B1 | 11/1991 | European Pat. Off. . |
| 0705584A1 | 4/1996 | European Pat. Off. . |
| 0 710 471 A1 | 5/1996 | European Pat. Off. . |
| 0 710 472 A1 | 5/1996 | European Pat. Off. . |
| 3 343 622 A1 | 6/1985 | Germany . |
| 6-910 A | 1/1994 | Japan . |
| 2 171 915 | 9/1986 | United Kingdom . |
| 2241871 | 9/1991 | United Kingdom . |
| 2264258 | 8/1993 | United Kingdom . |
| 94/23107 | 10/1994 | WIPO . |
| 94/23947 | 10/1994 | WIPO . |
| 95/25496 | 9/1995 | WIPO . |
| WO 95/26878 A1 | 10/1995 | WIPO . |
| 96/09165 | 3/1996 | WIPO . |
| WO 96/14034 A1 | 5/1996 | WIPO . |
| WO 96/14037 A1 | 5/1996 | WIPO . |
| WO 96/14038 | 5/1996 | WIPO . |

ABSORBENT ARTICLE HAVING A BREATHABILITY GRADIENT

BACKGROUND OF THE INVENTION

1. Field of the Invention

The present invention relates to an absorbent article for absorbing body fluids and exudates, such as urine. More particularly, the present invention relates to absorbent garments, such as disposable diapers and adult incontinence garments, which are configured to absorb body exudates while also helping to provide reduced skin hydration.

2. Description of the Related Art

Many known diaper configurations employ absorbent materials located between a liquid previous topsheet and a vapor and liquid impermeable backsheet. Such backsheets are well suited to prevent the migration of liquid waste from the absorbent materials to the outer garments of a wearer. Unfortunately, the use of liquid and vapor impermeable backsheets can result in a relatively high degree of humidity within the diaper when in use. This may result in relatively high skin hydration levels and may lead to the onset of diaper rash.

In order to reduce the humidity level within diapers, breathable polymer films have been employed as outer covers for absorbent garments, such as disposable diapers. The breathable films are typically constructed with micropores to provide desired levels of liquid impermeability and vapor permeability. Other disposable diaper designs have been arranged to provide some level of breathability at the leg cuff regions of the diaper. Still other disposable diaper designs have been arranged to provide humidity transfer regions in the form of breathable panels in otherwise vapor-impermeable backsheets or to employ perforated regions to help ventilate the garment.

Conventional absorbent articles, such as those described above, have not been completely satisfactory. For example, articles which employ a microporous outer cover can exhibit a cold and clammy feeling when the garment is wetted and moisture is evaporating through the microporous film. The articles which employ perforated films or breathable panels can exhibit excessive leakage of liquids from the article and can excessively soil the wearer's outer garments. In addition, when the absorbent material of the article becomes loaded with liquid, the wet absorbent can block the escape of moisture from the wearers skin. Such absorbent garment designs have not been able to sufficiently reduce the hydration of the wearer's skin. As a result, the wearers skin has remained susceptible to rashes, abrasion and irritation.

SUMMARY OF THE INVENTION

In response to the difficulties and problems discussed above, a new disposable absorbent article which has a breathability gradient has been discovered.

As used herein, reference to "humidity transfer" refers to the transfer of water vapor from the interior of a diaper, when in use on a wearer, to the exterior of the diaper (ambient atmosphere).

As used herein, a substantially liquid impermeable material is constructed to provide a hydrohead of at least about 60 cm (centimeters), desirably at least about 80 cm, and more desirably at least about 100 cm. A suitable technique for determining the hydrohead value is the Hydrostatic Pressure Test which is described in further detail herein below.

As used herein, a substantially vapor permeable material is constructed to provide a water vapor transmission rate (WVTR) of at least about 100 g/sq.m/24 hr, desirably at least about 250 g/sq.m/24 hr, and more desirably at least about 500 g/sq.m/24 hr. A suitable technique for determining the WVTR value is the WVTR Test which is described in further detail herein below.

In one aspect, the present invention relates to an absorbent article which defines a garment facing surface, a body facing surface, a front waistband section, a rear waistband section and an intermediate section which interconnects the front and rear waistband sections. The absorbent article comprises a first zone of vapor permeability which is located on the garment facing surface and which defines a water vapor transmission rate of from about 100 to about 2500 g/sq.m/24 hr. The absorbent article further comprises a second zone of vapor permeability which is located on the garment facing surface and which defines a water vapor transmission rate of at least about 3000 g/sq.m/24 hr. The first zone of vapor permeability may define an area which is at least about 75 percent of the garment facing surface of the absorbent article. The first zone of vapor permeability may further define a width which is less than a width of the absorbent article and the second zone of vapor permeability may extend beyond the first zone of vapor permeability thereby providing a breathability gradient across the width of the absorbent article.

In another aspect, the present invention relates to an absorbent article which comprises a vapor permeable backsheet which includes a first zone of vapor permeability which defines a water vapor transmission rate of at least about 100 g/sq.m/24 hr and a second zone of vapor permeability which defines a water vapor transmission rate of at least about 3000 g/sq.m/24 hr. The absorbent article further comprises a liquid permeable topsheet which is positioned in facing relation with the backsheet and an absorbent body located between the backsheet and the topsheet. In a particular aspect, the first zone of vapor permeability covers at least about 75 percent of a garment side of the absorbent body.

In still another aspect, the present invention relates to an absorbent article which comprises a substantially liquid impermeable, vapor permeable backsheet which defines a water vapor transmission rate of at least about 1500 g/sq.m/24 hr, a liquid permeable topsheet which is positioned in facing relation with the backsheet, and an absorbent body which is located between the backsheet and the topsheet. The absorbent article further comprises a vapor permeable barrier layer which is smaller in size than the backsheet and which is located between the absorbent body and the backsheet. The combination of the vapor permeable barrier layer and the vapor permeable backsheet defines a water vapor transmission rate of from about 100 to about 2500 g/sq.m/24 hr. In a particular aspect, the substantially liquid impermeable, vapor permeable backsheet is constructed to provide a hydrohead of at least 60 cm. The vapor permeable barrier layer may define a water vapor transmission rate of from about 100 to about 5000 g/sq.m/24 hr.

The present invention advantageously provides an improved absorbent article which substantially reduces the hydration of the wearer's skin when compared to conventional absorbent articles. Thus, wearer's of absorbent articles made according to the present invention should have a reduced incidence of skin irritation or rash.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence garments, training pants, and the like.

Figure 1:
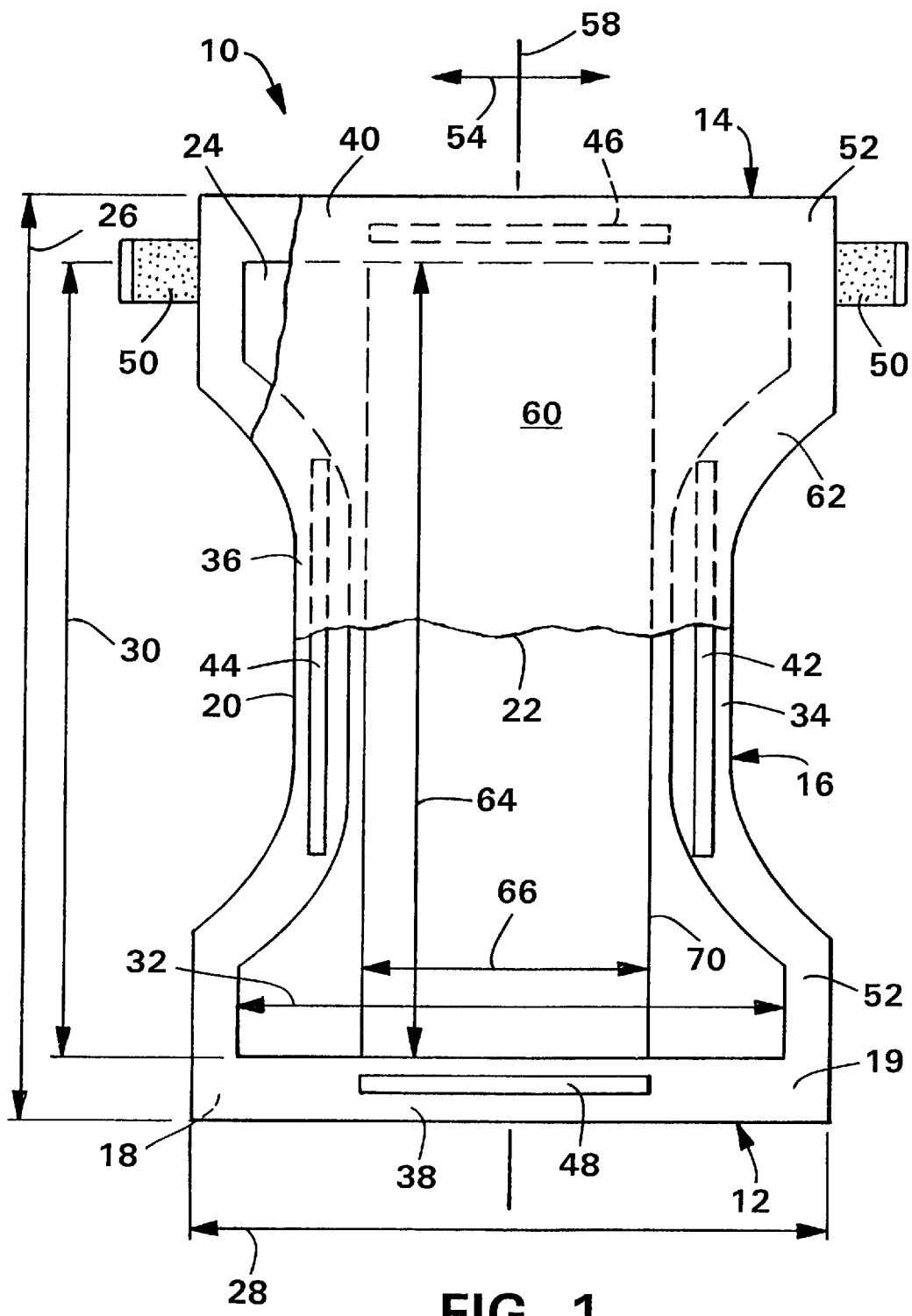
FIG. 1 representatively shows a partially cutaway, top plan view of an absorbent article according to one embodiment of the invention.
Figure 2:
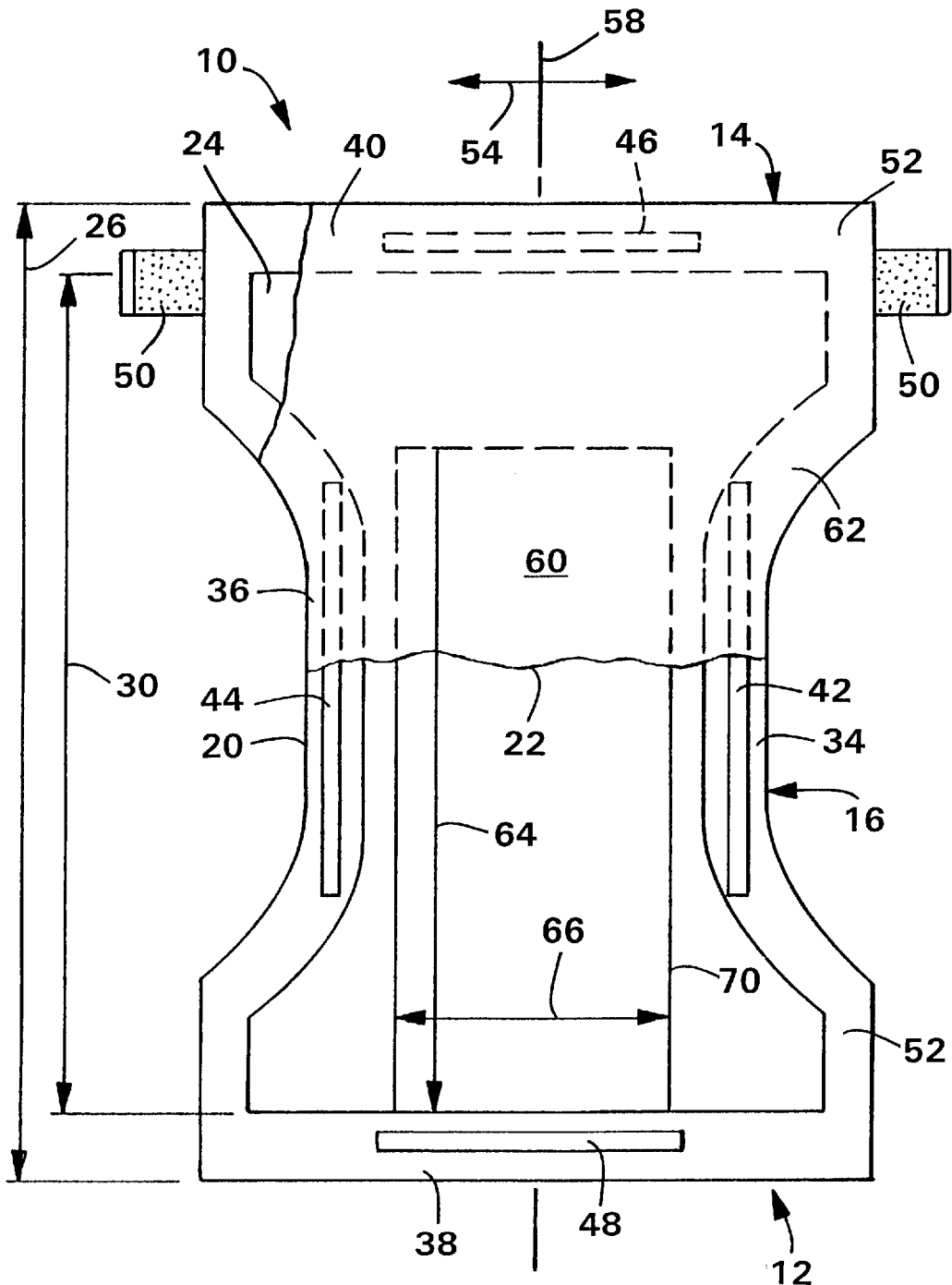
FIG. 2 representatively shows a partially cutaway, top plan view of an absorbent article according to a second embodiment of the invention.

With reference to FIGS. 1 and 2, an integral absorbent garment article, such as the disposable diaper 10, generally defines a front waistband section 12, a rear waistband section 14, and an intermediate section 16 which interconnects the front and rear waistband sections. The front and rear waistband sections include the general portions of the article which are constructed to extend substantially over the wearer's front and rear abdominal regions, respectively, during use. The intermediate section of the article includes the general portion of the article which is constructed to extend through the wearer's crotch region between the legs. The absorbent article also includes a garment facing surface 18 and a body facing surface 19.

The absorbent article includes a substantially liquid impermeable, vapor permeable backsheet 20, a liquid permeable topsheet 22 positioned in facing relation with the backsheet 20, and an absorbent body 24, such as an absorbent pad, which is located between the backsheet and the topsheet. The absorbent body 24 overlays at least a portion of the backsheet 20. The backsheet 20 has a length 26 and a width 28 which, in the illustrated embodiment, coincides with the length and width of the diaper 10. The absorbent body 24 generally has a length 30 and width 32 which are less than the length 26 and width 28 of the backsheet 20, respectively. Marginal portions of the diaper 10, such as marginal sections of the backsheet 20, may extend past the terminal edges of the absorbent body 24. In the illustrated embodiments, for example, the backsheet 20 extends outwardly beyond the terminal marginal edges of the absorbent body 24 to form side margins 34 and 36 and end margins 38 and 40 of the diaper 10. The topsheet 22 is generally coextensive with the backsheet 20 but may optionally cover an area which is larger or smaller than the area of the backsheet 20, as desired.

The absorbent article further includes a zone of low vapor permeability 60 and a zone of high vapor permeability 62. In the illustrated embodiments, for example, the absorbent article may include a zone of low vapor permeability 60 which extends along a longitudinal centerline 58 of the article and has a length 64 and width 66 which are less than the length 26 and width 28 of the backsheet 20. In such a configuration, the zone of high vapor permeability 62 generally extends beyond the edges of the zone of low vapor permeability 60 to the outermost edges of the backsheet 20 of the absorbent article providing a breathability gradient across the length 26 and width 28 of the diaper. The zones of vapor permeability are configured to enhance the breathability of the absorbent article to reduce the hydration of the wearer's skin during use without allowing excessive condensation of vapor, such as urine, on the garment facing surface of the backsheet 20 which can undesirably dampen the wearer's clothes.

To provide improved fit and to help reduce leakage of body exudates from the diaper 10, the diaper side margins and end margins may be elasticized with suitable elastic members, such as single or multiple strands of elastic. The elastic strands may be composed of natural or synthetic rubber and may optionally be heat shrinkable or heat elasticizable. Elastic members 42 and 44 are constructed to operably gather and shirr the side margins 34 and 36 of the diaper 10 to provide elasticized leg bands which can closely fit around the legs of the wearer to reduce leakage and provide improved comfort and appearance. Similarly, waist elastic members 46 and 48 can be employed to elasticize the end margins 38 and 40 of the diaper 10 to provide elasticized waistbands. The waist elastics are configured to operably gather and shirr the waistband sections to provide a resilient, comfortably close fit around the waist of the wearer. In FIGS. 1 and 2, the elastic members are illustrated in their uncontracted, stretched condition for the purpose of clarity.

Fastening means, such as adhesive tapes 50, are employed to secure the diaper on a wearer. Alternatively, other fastening means, such as buttons, pins, snaps, hook-and-loop fasteners, mushroom-and-loop fasteners, or the like, may be employed.

The illustrated embodiment of the diaper 10 includes ear portions 52 which extend laterally along the diaper cross-direction 54 and are positioned at least at the rear waistband section 14 of the diaper 10. Ear portions 52 may also be located at the front waistband section 12 of the diaper. The ear portions may be integral with the backsheet 20 or may comprise separate sections which are composed of the same or different material than the backsheet 20 and are suitably assembled and attached to the backsheet 20. The ear portions 52 typically provide extensions of the diaper waistband suitable for completely encircling the waist of the wearer during use.

The diaper 10 may be of various suitable shapes. For example, the diaper may have an overall rectangular shape, T-shape or an approximately hour-glass shape. In the shown embodiment, the diaper 10 has a generally I-shape. Other suitable diaper components which may be incorporated on absorbent articles of the present invention include containment flaps, waist flaps, elastomeric side panels, and the like.

Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. patent application Ser. No. 08/096,654 filed Jul. 22, 1993, in the name of Hanson et al., the disclosures of which are herein incorporated by reference to the extent they are consistent herewith.

The various components of the diaper 10 are integrally assembled together employing various types of suitable attachment means, such as adhesive, sonic bonds, thermal bonds or combinations thereof. In the shown embodiment, for example, the topsheet 22 and backsheet 20 are assembled to each other and to the absorbent body 24 with lines of adhesive, such as a hot melt, pressure-sensitive adhesive. Similarly, other diaper components, such as the elastic members 42, 44, 46 and 48, and the fastening members 50, may be assembled into the diaper article by employing the above-identified attachment mechanisms.

The topsheet 22, as representatively illustrated in FIGS. 1 and 2, suitably presents a bodyfacing surface which is compliant, soft feeling, and nonirritating to the wearer's skin. Further, the topsheet 22 may be less hydrophilic than the absorbent body 24, to present a relatively dry surface to the wearer, and may be sufficiently porous to be liquid permeable, permitting liquid to readily penetrate through its thickness. A suitable topsheet 22 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet 22 is suitably employed to help isolate the wearers skin from liquids held in the absorbent body 24.

Various woven and nonwoven fabrics can be used for the topsheet 22. For example, the topsheet may be composed of a meltblown or spunbonded web of polyolefin fibers. The topsheet may also be a bonded-carded web composed of natural and/or synthetic fibers. The topsheet may be composed of a substantially hydrophobic material, and the hydrophobic material may, optionally, be treated with a surfactant or otherwise processed to impart a desired level of wettability and hydrophilicity. In a particular embodiment of the present invention, the topsheet 22 comprises a nonwoven, spunbond, polypropylene fabric composed of about 2.8–3.2 denier fibers formed into a web having a basis weight of about 22 grams per square meter and a density of about 0.06 gram per cubic centimeter. The fabric is surface treated with about 0.28 weight percent of a surfactant commercially available from Rohm and Haas Co. under the trade designation Triton X-102.

The absorbent body 24 of the diaper 10, as representatively illustrated in FIGS. 1 and 2, may suitably comprise a matrix of hydrophilic fibers, such as a web of cellulosic fluff, mixed with particles of a high-absorbency material commonly known as superabsorbent material. In a particular embodiment, the absorbent body 24 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. Alternatively, the absorbent body 24 may comprise a laminate of fibrous webs and superabsorbent material or other suitable means of maintaining a superabsorbent material in a localized area.

The absorbent body 24 may have any of a number of shapes. For example, the absorbent core may be rectangular, I-shaped, or T-shaped. It is generally preferred that the absorbent body 24 be narrower in the intermediate section than in the front or rear waistband sections of the diaper 10.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body 24.

Optionally, a substantially hydrophilic tissue wrapsheet (not illustrated) may be employed to help maintain the integrity of the airlaid fibrous structure of the absorbent body 24. The tissue wrap sheet is typically placed about the absorbent body over at least the two major facing surfaces thereof and composed of an absorbent cellulosic material, such as creped wadding or a high wet-strength tissue. In one aspect of the invention, the tissue wrap can be configured to provide a wicking layer which helps to rapidly distribute liquid over the mass of absorbent fibers comprising the absorbent body.

The backsheet 20 of the diaper 10, as representatively illustrated in FIGS. 1 and 2, is composed of a substantially liquid impermeable material which is also substantially vapor permeable. In particular, the backsheet 20 is constructed to provide a hydrohead value of at least about 60 cm, desirably at least about 80 cm, and more desirably at least about 100 cm when subjected to the Hydrostatic Pressure Test. Materials which have hydrohead values less than those above undesirably result in the strike through of liquids, such as urine, during use. Such fluid strike through can undesirably result in a damp, clammy feeling on the backsheet 20 during use. The backsheet 20 is further constructed to be substantially permeable to at least water vapor and has a water vapor transmission rate of at least about 3000 g/sq.m/24 hr. and desirably at least about 5000 g/sq.m/24 hr. Materials which have a water vapor transmission rate less than those above do not allow a sufficient amount of humidity transfer and undesirably result in increased levels of skin hydration.

The backsheet 20 may be composed any suitable materials which either directly provide the above desired levels of liquid impermeability and vapor permeability or, in the alternative, materials which can be modified or treated in some manner to provide such levels. In one embodiment, the backsheet 20 may be a nonwoven fibrous web constructed to provide the required level of liquid impermeability. For example, a nonwoven web composed of spunbonded or meltblown polymer fibers may be selectively treated with a water repellent coating or laminated with a liquid impermeable polymer film to provide the backsheet 20. In a particular embodiment of the invention, the backsheet 20 may comprise a nonwoven web composed of a plurality of randomly deposited hydrophobic thermoplastic meltblown fibers which are sufficiently bonded or otherwise connected to one another to provide a substantially vapor permeable and substantially liquid impermeable web. The backsheet 20 may also comprise a vapor permeable nonwoven layer which has been partially coated or otherwise configured to provide liquid impermeability in selected areas.

An example of a suitable material for the backsheet 20 is described in commonly owned, copending U.S. patent application Ser. No. 08/223,210 filed Apr. 5, 1994, in the name of Bradley et al. Other suitable materials for the backsheet 20 include those described in U.S. Pat. No. 4,713,068 issued Dec. 15, 1987, to Wang et al.; U.S. Pat. No. 4,758,239 issued Jul. 19, 1988, to Yeo et al.; U.S. Pat. No. 4,818,600 issued Apr. 4, 1989, to Braun et al.; and U.S. Pat. No. 4,828,556 issued May 9, 1989, to Braun et al., the disclosures of which are herein incorporated by reference to the extent they are consistent herewith.

The zones of low vapor permeability 60 and high vapor permeability 62 of the absorbent article, as representatively illustrated in FIG. 1, are configured to enhance the breathability of the article to reduce the hydration of the wearer's skin during use without allowing excessive condensation of vapor, such as urine, on the garment facing surface of the backsheet 20 which can dampen the wearer's clothes. The zone of high vapor permeability 62 is designed to provide the maximum humidity transfer from the absorbent article while the zone of low vapor permeability 60 is designed to reduce the risk of excessive condensation of vapor on the garment facing surface of the backsheet while still providing at least some level of humidity transfer. Accordingly, the zone of low vapor permeability 60 is generally positioned in the area of the absorbent article which is intended to receive and hold the majority of the body exudates while the zone of high vapor permeability 62 is generally positioned in the side and end margins of the absorbent article.

The zone of high vapor permeability 62 is generally that area of the diaper in which water vapor can transfer from the inside of the diaper, when in position on a wearer, to the outside of the diaper with relative ease. That is, it is the area over which humidity can transfer from the topsheet 22, through any intervening layer of material, and out the vapor permeable backsheet 20. For example, the zone of high vapor permeability 62 may include the entire area in which the topsheet 22 is in direct face-to-face overlapping relationship with the vapor permeable backsheet 20. The zone of low vapor permeability effectively prevents the transfer of liquids and excessive vapor from the interior of the diaper, when in use, through the vapor permeable backsheet in those areas of the diaper where at least a portion of the absorbent body 24 overlays the backsheet, such as in the intermediate section 16 of the diaper 10. The zone of low vapor permeability 60 may also prevent the transfer of a high level of humidity from the interior of the diaper. In many instances this is desirable since a high degree of transfer of humidity across the entire surface of the diaper has been found to produce a clammy feeling on the outer surface of the diaper which many consumers perceive in a negative manner. Thus, the humidity transfer from the interior of the diaper to the ambient atmosphere (exterior of the diaper) occurs generally in the zone of relatively high vapor permeability 62 but can also occur in the zone of relatively low vapor permeability 60 to a limited degree.

The zones of low and high vapor permeability are located on the absorbent article to provide the desired humidity transfer. The zones of low and high vapor permeability may have any desired configuration including rectangular, hourglass, oval, and the like, and may also include selected strips or multiple zones which may be intermittently located.

For example, in the illustrated embodiments, the absorbent article includes a zone of low vapor permeability 60 having a generally rectangular configuration. As representatively illustrated, the zone of low vapor permeability extends along a longitudinal centerline 58 of the article and has a length 64 and width 66 which are less than the length 26 and width 28 of the backsheet 20. In such a configuration, the zone of high vapor permeability 62 generally extends beyond the edges of the zone of low vapor permeability 60 to the outermost edges of the backsheet 20 of the absorbent article thereby providing a breathability gradient across the length 26 and width 28 of the diaper. The zones of low and high vapor permeability 60 and 62 may cover the entire backsheet 20 or only a portion thereof. In the illustrated embodiments, the zones of low and high vapor permeability cover the entire exposed or body facing surface of the backsheet 20.

The zones of low and high vapor permeability may have any desired dimensions which effectively provides improved humidity transfer while preventing excessive condensation of vapor from the absorbent body 24 through and onto the garment facing surface of the backsheet 20. In the embodiment illustrated in FIG. 1, the length 64 of the zone of low vapor permeability 60 is substantially the same as the length 30 of the absorbent body 24 to reduce the risk of excessive condensation on the backsheet 20 in this area. Whereas, in the embodiment illustrated in FIG. 2, the length 64 of the zone of low vapor permeability 60 is somewhat less than the length of the absorbent body 24. In such a configuration, it is desirable that the zone of low vapor permeability 60 cover at least a substantial portion of the absorbent body 24 in the front section 12 of the absorbent article for improved performance. In both of the illustrated embodiments, the width 66 of the zone of low vapor permeability 60 is somewhat less than the width of the absorbent body 24 in the intermediate section 16 of the absorbent article. However, the zone of low vapor permeability 60 may extend completely across the absorbent body 24 or the absorbent article in the intermediate section 16 if desired. In a particular embodiment, it is desirable that the zone of low vapor permeability 60 have a length 64 which is at least about 75 percent of the length 30 of the absorbent body 24 and a width 66 which is at least about 100 percent of the width of the absorbent body 24 as measured at the narrowest portion of the intermediate section 16 of the article.

The zone of relatively low vapor permeability 60 generally has an area which corresponds to at least a portion of the area of the garment side of the absorbent body 24 to effectively prevent excessive condensation of vapor on the garment facing surface of the backsheet 20. For example, on a medium-sized diaper adapted to fit an infant weighing from 22–35 pounds, the zone of relatively low vapor permeability 60 generally has an area of at least about 200 square centimeters and desirably at least about 300 square centimeters. Desirably, the zone of low vapor permeability 60 has an area of at least about 75 percent, desirably at least about 90 percent, and more desirably at least about 100 percent of the garment side of the absorbent body 24 of the diaper 10. Moreover, the zone of low vapor permeability 60 desirably has an area of at least about 30 percent and more desirably at least about 50 percent of the total exposed area of the backsheet 20 of the diaper 10. For example, the zone of relatively low vapor permeability 60 may have an area of from about 30 to about 85 percent of the total exposed area of the backsheet 20 of the diaper 10. When the area of the zone of low vapor permeability 60 is too small, the diaper 10 may exhibit an undesirable amount of condensation of vapor on the exposed, garment facing surface of the backsheet 20 resulting in a clammy feeling on the outer surface of the diaper which many consumers perceive in a negative manner. Whereas, when the area of the zone of low vapor permeability 60 is too large, the diaper 10 may exhibit a low level of humidity transfer resulting in high levels of skin hydration, skin irritation and rash.

The zone of relatively high vapor permeability 62 generally has an area which corresponds to at least the side margins 34 and 36 and end margins 38 and 40 of the diaper 10 to effectively allow the humidity transfer from the interior of the diaper to the ambient atmosphere. For example, on a medium-sized diaper adapted to fit an infant weighing from 22–35 pounds, the zone of high vapor permeability 62 generally has an area of at least about 100 square centimeters, desirably at least about 200 square centimeters, and more desirably from about 200 to about 800 square centimeters for improved performance. Desirably, the zone of high vapor permeability 62 has an area of at least about 15 percent and more desirably at least about 30 percent of the total exposed area of the backsheet 20 of the diaper 10. For example, the zone of relatively high vapor permeability 62 may have an area of from about 15 to about 70 percent of the total exposed area of the backsheet 20 of the diaper 10. When the area of the zone of high vapor permeability 62 is too small, the diaper 10 may exhibit a low level of humidity transfer resulting in skin irritation and rash. Whereas, when the area of the zone of high vapor permeability 62 is too high, the diaper 10 may exhibit an undesirable amount of vapor condensation.

The zone of low vapor permeability 60 of the diaper 10, as representatively illustrated in FIGS. 1 and 2, is constructed to provide a hydrohead value of at least about 60 cm, desirably at least about 80 cm, and more desirably at least about 100 cm when subjected to the Hydrostatic Pressure Test. Hydrohead values less than those above undesirably result in the strike through of liquids, such as urine, during use. The zone of low vapor permeability 60 is further constructed to be substantially permeable to at least water vapor and has a water vapor transmission rate of at least about 100 g/sq.m/24 hr., suitably from about 100 to about 2500 g/sq.m/24 hr, and desirably from about 1500 to about 2000 g/sq.m/24 hr. Applicants have discovered that when the zone of low vapor permeability has water vapor transmission rates greater than those above, excessive condensation of vapor appears on the garment facing surface of the backsheet which undesirably results in a damp feeling.

The zone of high vapor permeability 62 of the diaper 10, as representatively illustrated in is FIGS. 1 and 2, is constructed to provide a hydrohead value of at least about 60 cm, desirably at least about 80 cm, and more desirably at least about 100 cm when subjected to the Hydrostatic Pressure Test. Hydrohead values less than those above undesirably result in the strike through of liquids, such as urine, during use. The zone of high vapor permeability 62 is further constructed to be substantially permeable to at least water vapor and has a water vapor transmission rate of at least about 3000 g/sq.m/24 hr., suitably at least about 4000 g/sq.m/24 hr, and desirably at least about 5000 g/sq.m/24 hr. Water vapor transmission rates less than those above for the zone of high vapor permeability do not allow a sufficient amount of humidity transfer and undesirably result in increased levels of skin hydration.

The ratio of the water vapor transmission rates of the zone of high vapor permeability to the zone of low vapor permeability can be selectively controlled to provide the desired humidity transfer while still preventing excessive vapor condensation. Applicants have discovered that absorbent articles according to the present invention having a ratio of the water vapor transmission rates of the zone of high vapor permeability 62 to the zone of low vapor permeability 60 of at least about 1.1 and desirably from about 2.0 to about 2.5 have provided a breathability gradient across the article which has resulted in reduced levels of skin hydration during use.

The zones of low and high vapor permeability of the absorbent article of the present invention may be provided in a variety of ways. For example, the zones of low and high vapor permeability may be an integral portion of the backsheet 20 of the absorbent article or may be a separate component which may or may not be laminated to the backsheet 20. For example, a portion of a backsheet 20 having a high level of vapor permeability may be treated or coated with an adhesive or latex spray to provide the zone of low vapor permeability 60 in selected areas. Alternatively, a nonwoven material or polymeric film may be laminated to a portion of such a backsheet 20 to provide a two layer composite which provides the zones of low and high vapor permeability 60 and 62. For example, a nonwoven material such as those described above for use as the backsheet 20 or a polymeric film may be laminated to selected portions of the backsheet 20 to provide the zones of low and high vapor permeability 60 and 62. Such film materials are well known to those skilled in the art. The polymeric film may inherently possess the desired level of vapor permeability or may include perforations to provide the desired level of vapor permeability while preventing liquid strikethrough. The nonwoven material or polymeric film may be positioned between the absorbent body 24 and backsheet 20 while not being directly adhered to the backsheet 20 in any manner. Alternatively, the nonwoven material or polymeric film material may be adhered to the garment side of the absorbent body.

In the embodiments illustrated in FIGS. 1 and 2, the zones of low and high vapor permeability are provided by applying an adhesive in the desired pattern on the backsheet 20. Suitable adhesives include pressure sensitive hot melt adhesives which are known to those skilled in the art. A particularly suitable adhesive is an adhesive which is commercially available from the National Starch Company under the trade designation 34-5563. The adhesive is applied to the backsheet 20 by slot-coating. The amount of adhesive add-on may vary depending upon the type of adhesive and the desired level of liquid impermeability and vapor permeability of the low zone of vapor permeability 60. Adhesive add-on levels of from about 10 to about 30 gsm (grams per square meter) and desirably from about 15 to about 25 gsm have been found to provide the desired levels of vapor permeability and liquid impermeability for the zone of low vapor permeability 60.

The absorbent article of the present invention may optionally include a humidity transfer material (not shown) located between the topsheet 22 and the absorbent body 24 or between the backsheet 20 and the absorbent body 24. The humidity transfer material serves to facilitate the movement of air within the diaper. Specifically, it is hypothesized that the humidity transfer material serves as a conduit through which water vapor can move from the intermediate section of the interior of the diaper (when in use) to the side margins 34 and 36 and end margins 38 and 40 wherein the water vapor can be transferred out of the interior of the diaper through the zone of high vapor permeability and the vapor permeable backsheet 20. The humidity transfer material may suitably be formed from a nonwoven, (e.g., spunbond, meltblown or carded), woven, or knitted fibrous webs composed of natural fibers and/or synthetic polymeric fibers. Suitable fibers include, for example, acrylic fibers, polyolefin fibers, polyester fibers, or blends thereof. The humidity transfer material may also be formed from a porous foam material such as an open-celled polyolefin foam, a reticulated polyurethane foam, and the like. In a further aspect of the invention, the humidity transfer material includes a plurality of two or more individual layers positioned in facing adjacent relationship. For example, 2–5 individual layers may be located between the topsheet and the absorbent body and together collectively comprise the humidity transfer material. Examples of materials particularly well suited for use as a humidity transfer material are described in U.S. patent application Ser. No. 08/344,429 filed Nov. 23, 1994, in the name of Menard et al., the disclosure of which is hereby incorporated by reference to the extent it is consistent herewith.

The humidity transfer material may extend completely or partially over the zone of low vapor permeability 60. It is generally desired that the entire zone of low vapor permeability 60 be overlaid with the humidity transfer material. This allows for the maximum degree of humidity transfer. Further, the humidity transfer material may extend completely or partially over the adjacent surface of the absorbent body 24. The humidity transfer material is suitably located over the intermediate section 16 of the diaper and is substantially centered side-to-side with respect to the longitudinal centerline 58 of the diaper. The humidity transfer material suitably extends over about 35 to about 100 percent of the total length 26 of the backsheet 20. The humidity transfer material may extend over about 50 to about 100 percent of the width of the diaper as measured at the narrowest portion of the diaper intermediate section 16. It is generally preferred that the humidity transfer material extend at least partially into the zone of high vapor permeability 62.

TEST PROCEDURES

Hydrostatic Pressure Test

The Hydrostatic Pressure Test is a measure of the liquid barrier properties of a material. In general, the Hydrostatic Pressure Test determines the height of water (in centimeters) in a column which the material will support before a predetermined amount of water passes through. A material with a higher hydrohead value indicates it is a greater barrier to liquid penetration than a material having a lower hydrohead value. The Hydrostatic Pressure Test is performed according to Method 5514—Federal Test Methods Standard No. 191A.

Water Vapor Transmission Rate

A suitable technique for determining the WVTR (water vapor transmission rate) value of a material is as follows. For the purposes of the present invention, 3-inch diameter (76 millimeter) circular samples are cut from the test material and from a control material, Celguard® 2500 (Hoechst Celanese Corporation). Two or three samples are prepared for each material. Test cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred milliliters of distilled water are poured into each Vapometer cup, and each of the individual samples of the test materials and control material are placed across the open top area of an individual cup. Screw-on flanges are tightened to form a seal along the edges of the cups leaving the associated test material or control material exposed to the ambient atmosphere over a 62 millimeter diameter circular area (an open, exposed area of about 30 cm$^2$). The cups are then weighed, placed on a tray, and set in a forced air oven set at 100° F. (38° C.). The oven is a constant temperature oven with external air circulating through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary, test WVTR value is calculated as follows:

$$\text{Test } WVTR = \frac{[(\text{grams weight loss over 24 hours}) \times 7571]}{24} \text{ (g/m}^2\text{/24 hours)}$$

The relative humidity within the oven is not specifically controlled. Under predetermined set conditions of 100° F. and ambient relative humidity, the WVTR for Celguard 2500 has been determined to be 5000 g/m$^2$/24 hours. Accordingly, Celguard 2500 is run as a control sample with each test. Celguard 2500 is a 0.0025 cm thick film composed of a microporous polypropylene.

The following example is presented to provide a more detailed understanding of the invention. The specific materials and parameters are exemplary and are not intended to specifically limit the scope of the invention.

EXAMPLE 1

Material which could be used as the backsheet on absorbent articles such as diapers was produced. The liquid impermeable and vapor permeable backsheet comprised a spunbond/meltblown/spunbond (SMS) laminate material having a basis weight of about 50 grams per square meter (gsm). The SMS was formed from a meltblown polypropylene layer which has a basis weight of about 17 gsm and which was positioned between two spunbond polyethylene/polypropylene layers, each of which had a basis weight of about 17 gsm. The meltblown and spunbond layers were manufactured by Kimberly-Clark. The meltblown layer was composed of up to 5 weight percent polybutylene which was commercially available from Shell under the trade designation DP 8911 and the remainder polypropylene which was commercially available from Exxon under the trade designation 3546G. The spunbond layers were composed of up to 4 weight percent of a 50 percent concentration of titanium dioxide pigment which was commercially available from Ampacet under the trade designation Ampacet 41438. The remainder of the spunbond layers was composed of a 3 weight percent polyethylene/97 weight percent polypropylene copolymer which is commercially available from Shell under the trade designation 6D43. The meltblown layer provided from about 25 to about 35 weight percent of the SMS laminate material. The SMS material had a WVTR of about 5000 g/m$^2$/24 hours and was constructed to provide a hydrohead value of about 80 cm.

The material was configured to define a zone of low vapor permeability and a zone of high vapor permeability. The zone of low vapor permeability was formed by slot-coating an adhesive in a substantially uniform pattern on a surface of the material. The adhesive was commercially available from the National Starch Company under the trade designation 34-5563 and was applied at different levels of adhesive add-on from about 0 to about 25 gsm. The combination of the SMS material and the adhesive coating which provided the zone of low vapor permeability had a WVTR of about 4500 g/m²/24 hours at an adhesive add-on of about 5 gsm, a WVTR of about 3100 g/m²/24 hours at an adhesive add-on of about 10 gsm, a WVTR of about 2200 g/m²/24 hours at an adhesive add-on of about 15 gsm, and a WVTR of about 1100 g/m²/24 hours at an adhesive add-on of about 20 gsm.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

We claim:

1. An absorbent article which defines a garment facing surface, a body facing surface absorbent body, a front waistband section, a rear waistband section and an intermediate section which interconnects said front and rear waistband sections, said absorbent article wherein the improvement comprises:
   a) a first zone of vapor permeability which is located on said garment facing surface and which defines a water vapor transmission rate of from about 100 to about 2500 g/sq.m/24 hr as determined according to a Water Vapor Transmission Rate test set forth herein; and
   b) a second zone of vapor permeability which is located on said garment facing surface and which defines a water vapor transmission rate of at least about 3000 g/sq.m/24 hr as determined according to said Water Vapor Transmission Rate test.

2. An absorbent article according to claim 1 wherein said first zone of vapor permeability defines a water vapor transmission rate of from about 1500 to about 2000 g/sq.m/24 hr as determined according to said Water Vapor Transmission Rate test.

3. An absorbent article according to claim 1 wherein said second zone of vapor permeability defines a water vapor transmission rate of at least about 4000 g/sq.m/24 hr as determined according to said Water Vapor Transmission Rate test.

4. An absorbent article according to claim 1 wherein said first and second zones of vapor permeability include substantially said entire garment facing surface of said absorbent article.

5. An absorbent article according to claim 1 wherein said first zone of vapor permeability defines an area of at least about 200 square centimeters.

6. An absorbent article according to claim 1 wherein said first zone of vapor permeability defines an area which is at least about 30 percent of said garment facing surface of said absorbent article.

7. An absorbent article according to claim 1 wherein said second zone of vapor permeability defines an area of at least about 100 square centimeters.

8. An absorbent article according to claim 1 wherein said second zone of vapor permeability defines an area which is at least about 15 percent of said garment facing surface of said absorbent article.

9. An absorbent article according to claim 1 wherein said absorbent article defines a longitudinal centerline and said first zone of vapor permeability is centered about and extends along said longitudinal centerline.

10. An absorbent article according to claim 9 wherein said first zone of vapor permeability defines a width which is less than a width of said absorbent article and said second zone of vapor permeability extends beyond said first zone of vapor permeability thereby providing a breathability gradient across said width of said absorbent article.

11. An absorbent article according to claim 1 and further comprising an absorbent body located between said garment facing surface and said body facing surface wherein said first zone of vapor permeability covers at least about 75 percent of a garment side of said absorbent body.

12. An absorbent article according to claim 11 wherein said first zone of vapor permeability covers said entire garment side of said absorbent body.

13. An absorbent article according to claim 11 wherein said first zone of vapor permeability defines a width which is at least about 100 percent of a width of said absorbent body as measured at a narrowest portion of said intermediate section of said article.

14. An absorbent article which comprises:
   a) a vapor permeable backsheet which includes a first zone of vapor permeability which defines a water vapor transmission rate of at least about 100 g/sq.m/24 hr as determined according to a Water Vapor Transmission Rate test set forth herein and a second zone of vapor permeability which defines a water vapor transmission rate of at least about 3000 g/sq.m/24 hr as determined according to said Water Vapor Transmission Rate test;
   b) a liquid permeable topsheet which is positioned in facing relation with said backsheet; and
   c) an absorbent body located between said backsheet and said topsheet.

15. An absorbent article according to claim 14 wherein said vapor permeable backsheet is substantially liquid impermeable.

16. An absorbent article according to claim 14 wherein said vapor permeable backsheet is constructed to provide a hydrohead value of at least about 60 cm as determined according to a Hydrostatic Pressure Test set forth herein.

17. An absorbent article according to claim 14 wherein said vapor permeable backsheet is constructed to provide a hydrohead value of at least about 80 cm as determined according to a Hydrostatic Pressure Test set forth herein.

18. An absorbent article according to claim 14 wherein said first zone of vapor permeability defines a water vapor transmission rate of from about 100 to about 2500 g/sq.m/24 hr as determined according to said Water Vapor Transmission Rate test.

19. An absorbent article according to claim 14 wherein said second zone of vapor permeability defines a water vapor transmission rate of at least about 4000 g/sq.m/24 hr as determined according to said Water Vapor Transmission Rate test.

20. An absorbent article according to claim 14 wherein said first zone of vapor permeability defines an area which is from about 30 to about 85 percent of an area of a garment facing surface of said backsheet.

21. An absorbent article according to claim 14 wherein said second zone of vapor permeability defines an area which is at least about 15 percent of an area of a garment facing surface of said backsheet.

22. An absorbent article according to claim 14 wherein said absorbent article defines a longitudinal centerline and said first zone of vapor permeability extends along said longitudinal centerline.

23. An absorbent article according to claim 22 wherein said first zone of vapor permeability is centered about said longitudinal centerline and defines a width which is at least about 100 percent of a width of said absorbent body as measured at a narrowest portion of said intermediate section of said article.

24. An absorbent article according to claim 14 wherein said first zone of vapor permeability covers at least about 75 percent of a garment side of said absorbent body.

25. An absorbent article according to claim 14 wherein said first zone of vapor permeability is defined by a portion of said vapor permeable backsheet which overlays said absorbent body and said second zone of vapor permeability is defined by a portion of said vapor permeable backsheet which extends beyond an outer perimeter of said absorbent body.

26. An absorbent article according to claim 14 wherein said vapor permeable backsheet comprises a nonwoven material.

27. An absorbent article according to claim 14 wherein said vapor permeable backsheet comprises a spunbond meltblown spunbond laminate.

28. An absorbent article according to claim 14 wherein said vapor permeable backsheet includes an outer layer and a barrier layer which is smaller than said outer layer and which is positioned in facing relation with said outer layer.

29. An absorbent article according to claim 28 wherein said first zone of vapor permeability is provided by a portion of said backsheet which includes both said outer layer and said barrier layer.

30. An absorbent article according to claim 28 wherein said second zone of vapor permeability is provided by a portion of said outer layer which extends beyond said barrier layer.

31. An absorbent article according to claim 28 wherein said outer layer is a nonwoven material which defines a water vapor transmission rate of at least about 3000 g/sq.m/24 hr as determined according to said Water Vapor Transmission Rate test and which is constructed to provide a hydrohead value of at least about 60 cm as determined according to a Hydrostatic Pressure Test set forth herein.

32. An absorbent article according to claim 28 wherein said barrier layer defines a water vapor transmission rate of from about 100 to about 2500 g/sq.m/24 hr as determined according to said Water Vapor Transmission Rate test and which is constructed to provide a hydrohead value of at least about 60 cm as determined according to a Hydrostatic Pressure Test as set forth herein.

33. An absorbent article according to claim 28 wherein said barrier layer is an adhesive coating which is applied to said outer layer and wherein a combination of said barrier layer and said outer layer defines a water vapor transmission rate of at least about 100 g/sq.m/24 hr as determined according to said Water Vapor Transmission Rate test.

34. An absorbent article which comprises:
a) a substantially liquid impermeable, vapor permeable backsheet which defines a water vapor transmission rate of at least about 3000 g/sq.m/24 hr as determined according to a Water Vapor Transmission Rate test as set forth herein;
b) a liquid permeable topsheet which is positioned in facing relation with said backsheet;
c) an absorbent body which is located between said backsheet and said topsheet; and
d) a vapor permeable barrier layer which is smaller in size than said backsheet and which is located between said absorbent body and said backsheet wherein a combination of said vapor permeable backsheet and said vapor permeable barrier layer defines a water vapor transmission rate of from about 100 to about 2500 g/sq.m/24 hr as determined according to said Water Vapor Transmission Rate test.

35. An absorbent article according to claim 34 wherein said vapor permeable backsheet defines a water vapor transmission rate of at least about 4000 g/sq.m/24 hr as determined according to said Water Vapor Transmission Rate test.

36. An absorbent article according to claim 34 wherein said substantially liquid impermeable, vapor permeable backsheet is constructed to provide a hydrohead value of at least about 60 cm as determined according to a Hydrostatic Pressure Test as set forth herein.

37. An absorbent article according to claim 34 wherein said vapor permeable barrier layer defines a water vapor transmission rate of from about 100 to about 2500 g/sq.m/24 hr as determined according to said Water Vapor Transmission Rate test.

38. An absorbent article according to claim 34 whereins aid vapor permeable barrier layer is substantially liquid impermeable.

39. An absorbent article according to claim 34 wherein said combination of said vapor permeable backsheet and said vapor permeable barrier layer provides a hydrohead value of at least about 80 cm as determined according to a Hydrostatic Pressure Test as set forth herein.

40. An absorbent article according to claim 34 wherein said combination of said vapor permeable backsheet and said vapor permeable barrier layer defines a water vapor transmission rate of from about 1500 to about 2000 g/sq.m/24 hr as determined according to said Water Vapor Transmission Rate test.

41. An absorbent article according to claim 34 wherein said combination of said vapor permeable backsheet and said vapor permeable barrier layer provides a hydrohead value of at least about 100 cm as determined according to a Hydrostatic Pressure Test as set forth herein.

42. An absorbent article according to claim 34 wherein said vapor permeable barrier layer defines an area which is at least about 30 percent of an area of a garment facing surface of said vapor permeable backsheet.

43. An absorbent article according to claim 34 wherein said vapor permeable barrier layer defines an area of at least about 200 square centimeters.

44. An absorbent article according to claim 34 wherein said vapor permeable barrier layer is centered about and extends lengthwise along a longitudinal centerline of said absorbent article.

45. An absorbent article according to claim 34 wherein said vapor permeable barrier layer defines a width which is substantially the same as a width of a narrowest portion of said absorbent body.

46. An absorbent article according to claim 34 wherein said vapor permeable barrier layer covers at least about 75 percent of a garment side of said absorbent body.

47. An absorbent article according to claim 34 wherein said vapor permeable backsheet comprises a nonwoven material.

48. An absorbent article according to claim 34 wherein said vapor permeable backsheet comprises a spunbond meltblown spunbond laminate.

49. An absorbent article according to claim 34 wherein said vapor permeable barrier layer comprises a nonwoven material.

50. An absorbent article according to claim 34 wherein said vapor permeable barrier layer remains unadhered to said vapor permeable backsheet.

51. An absorbent article according to claim 34 wherein said vapor permeable barrier layer defines a width which is less than a width of said vapor permeable backsheet in at least a portion of said intermediate section of said absorbent article thereby providing a breathability gradient across said width of said backsheet.

* * * * *